United States Patent
Friesen et al.

[11] Patent Number: 5,225,174
[45] Date of Patent: Jul. 6, 1993

[54] NITROGEN SORPTION

[75] Inventors: Dwayne T. Friesen; Walter C. Babcock; David J. Edlund; Warren K. Miller, all of Bend, Oreg.

[73] Assignee: Bend Research, Inc., Bend, Oreg.

[21] Appl. No.: 805,586

[22] Filed: Dec. 11, 1991

[51] Int. Cl.⁵ .................. C01B 21/00; C01B 13/00
[52] U.S. Cl. .................................... 423/235; 423/219; 423/351
[58] Field of Search ............ 423/351, 219, 235, 235 D

[56] References Cited

U.S. PATENT DOCUMENTS

| | | | |
|---|---|---|---|
| 4,457,898 | 7/1984 | Hill et al. | 423/219 |
| 4,605,475 | 8/1986 | Roberts et al. | 423/219 |
| 4,959,135 | 9/1990 | Zenner et al. | 423/219 |

FOREIGN PATENT DOCUMENTS 098157  1/1984  European Pat. Off. ............ 423/351

Primary Examiner—Gregory A. Heller
Attorney, Agent, or Firm—Chernoff, Vilhauer, McClung & Stenzel

[57] ABSTRACT

Nitrogen-sorbing and -desorbing compositions and methods of using the same are disclosed, which are useful for the selective separation of nitrogen from other gases, especially natural gas.

21 Claims, 5 Drawing Sheets

NITROGEN SORPTION

The government has rights in this invention pursuant to Contract No. DE-FG03-90ER80892 awarded by the Department of Energy.

BACKGROUND OF THE INVENTION

It has been estimated that 25% of the natural gas in the United States contains unacceptably high levels of the non-combustive contaminant nitrogen. Efforts to remove nitrogen from natural gas have included methane sorption and various techniques of cryogenic distillation such as liquification, turbocryogenic distillation, and "cold box" separation. All such efforts, though successful, have been relatively expensive and inefficient. There thus exists a need for a simple, efficient and low cost method of selectively removing nitrogen from natural gas. This need and others are met by the present invention, which is summarized and described in detail below.

SUMMARY OF THE INVENTION

The present invention comprises a nitrogen-absorbing and -desorbing composition (also referred to herein as a "sorption material") and a process of using the same to selectively remove nitrogen from other gases.

More particularly, the sorption composition comprises an organometallic complex either alone or in a relatively inert matrix wherein the matrix is either a liquid capable of dissolving the organometallic complex to $\geq 0.1M$, or a solid such as a polymer or a porous inorganic material, the organometallic complex comprising a transition metal and at least one ligand capable of providing five or six coordinating atoms. In some cases, one ligand is in the axial position and is termed an "axial base," the axial base being capable of providing a coordinating atom to the organometallic complex.

The process comprises absorbing nitrogen from a nitrogen-containing feed stream typically containing substantially no oxygen, no carbon monoxide, no thiols and no sulfides by contacting the feed stream with the nitrogen-sorption and -desorption material, followed by desorbing nitrogen from the sorption material. Desorption may be accomplished by temperature swing, pressure swing or a combination of the two. As the nitrogen-sorption capacity decreases over time due to decomposition of the sorption material, an optional step to improve efficiency is regeneration of its nitrogen-sorption capacity by various methods.

DETAILED DESCRIPTION OF THE INVENTION

Figure 1:
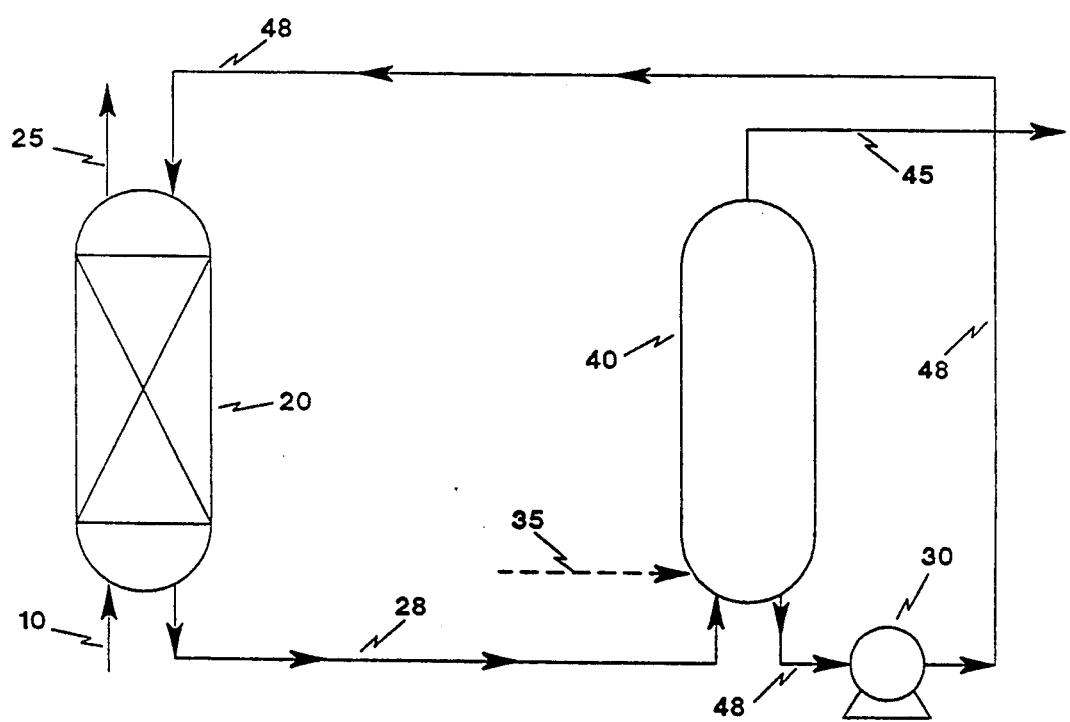
FIG. 1 is a schematic of an exemplary pressure swing absorption/desorption process of the present invention.

According to the present invention, there is provided a nitrogen-absorbing and -desorbing material having utility in the selective removal of nitrogen from a broad class of other gases and specific utility in the removal of nitrogen from naturally-occurring natural gas mixtures.

According to a preferred embodiment, the sorption material is a solution having two essential components: a solvent and an organometallic complex that is soluble in the solvent to $\geq 0.1$ M. In general terms, the solvent should have the following properties:

hydrophilic, with a solubility parameter of $>20$ MP-a$^{\frac{1}{2}}$ and preferably $\geq 30$ MPa$^{\frac{1}{2}}$;

either incapable of coordinating or capable of only weakly coordinating with the nitrogen-binding site of the organometallic complex;

solubility of the organometallic complex therein should be $\geq 0.1M$, preferably $\geq 0.25M$, but not to exceed 95% of the solubility limit at the minimum operating temperature or that concentration that gives a solution viscosity $\leq 100$ cps at the operating temperature; and leads to a nitrogen-absorbing solution having an apparent nitrogen solubility of $\geq 0.1$ mol nitrogen per mol organometallic complex under the temperature and pressure of the nitrogen-containing feed as it enters a sorption column, and a substantially diminished nitrogen solubility under the temperature and pressure conditions prevailing in a desorption or stripping column.

Preferably, solvents should also have low volatility (b.p. 22 90° C.) and low toxicity.

Especially preferred solvents are water, dimethyl formamide (DMF), dimethyl acetamide (DMAc), formamide, N-methylformamide, glycerol, and glycols, such as ethylene glycol, propylene glycol, butylene glycol, dimethylethylene glycol and glycolic oligomers. Generally speaking, useful solvents include liquids or mixtures of the same which are preferably polar and hydrophilic, although non-polar liquids may be useful in some cases. Classes of useful solvents include lactams, sulfoxides, nitriles, amides, amines, esters, and ethers. In addition to the preferred solvents mentioned above, preferred examples of the broad classes of solvents include dimethylsulfoxide (DMSO), diethylsulfoxide, propylene carbonate, ethylene carbonate, benzonitrile, tributylphosphate (TBP) and other phosphates, alcohols, glycols, N-ethylformamide and nitrogen-containing heterocycles.

The complex comprises at least one, but not more than six, ligand(s) with a transition metal. The ligand(s) must be capable of providing five or six coordinating atoms to the transition metal. The ligand(s) may be monodentate, bidentate, tridentate, tetradentate, pentadentate or hexadentate, or any combination of mono-, bi-, tri-, tetra-, penta- or hexadentate that forms a pentacoordinate or a hexacoordinate complex with the metal. The organometallic complex is preferably pentacoordinate, with bound nitrogen occupying the sixth coordination site. When the bound nitrogen displaces one of the ligands, the organometallic complex may be hexacoordinate.

Preferred transition metals that comprise part of the organometallic complex include the metals of Groups 7, 8 and 9, such as the early and third row transition metals Mo(O), W(O), Re(I), Re(II), Ru(II), Fe(I), Fe(II), Co(O), Co(I), Os(II), Ir(I), Rh(I) and Mn(I). Other, less preferred transition metals include the metals of Groups 3, 4, 5 and 6. In general, those metals in Groups 3–5 with high oxophilicity and consequent susceptibility to irreversible oxidation should be avoided. Also, the dinitrogen complexes of the metals in Groups 3 through 6 are generally less preferred as they tend to be susceptible to chemical reaction (such as protonation) at the coordinated dinitrogen, which may lead to loss of nitrogen-binding capability of the organometallic complex.

The ligand that is trans to the coordinated nitrogen is termed the "axial base." Although the axial base is usually a different moiety than the equatorial ligands, it may in fact be the same. Exemplary axial bases are selected from halogens and pseudohalogens (such as hydride, cyanide and thiocyanate ions), arsines, stibnines, phosphines, phosphites, thiols, sulfides, nitrogen-containing bases, including heterocycles such as pyridines, imidazoles, amides and amines, sulfur-containing heterocycles such as thiophenes, carbon monoxide, nitrogen, nitrous oxide, hydroxy, alkoxy, aryloxy, hydrocarbon residues such as alkyl, aryl and olefinic groups. The axial base may also be covalently attached to one or more of the equatorial ligands through a bridging group. A tabulation of suitable axial bases is set forth in Table 1. Table 2 contains definitions of the R substituents of both the axial bases and the polydentate ligands, while Table 3 contains definitions of the R' bridging groups of the polydentate ligands.

TABLE 1

| Group No. | Structure | Classes of Compounds |
|---|---|---|
| 1 | R—Z—R with R above Z | amines, phosphines, arsines and stibnines where Z is N, P, As, Sb and R is —H or as defined in Table 2, Substituent Group A, B or C |
| 2 | R-S-R | thiols and sulfides where R is —H or as defined in Table 2, Substituent Group A, B or C, excluding H$_2$S and provided that when R is alkyl, it contains ≧4 carbons |
| 3 | N-heterocycle with R | N-contg. aromatic and nonaromatic heterocycles, including substituted and unsubstituted pyrroles, pyrazines, pyrimidines, pyridines and imidazoles where R is —H or as defined in Table 2, Substituent Group A, B or C |
| 4 | S-heterocycle with R | S-contg. aromatic heterocycles, including substituted and unsubstituted thiophenes, tetrahydrothiophenes and thiazoles where R is —H or as defined in Table 2, Substituent Group A, B or C |
| 5 | —OR | hydroxy, alkoxy and aryloxy where R is —H or as defined in Table 2, Substituent Groups A, B or C |
| 6 | —X | halogens and pseudohalogens where X is F$^\sim$, Cl$^\sim$, Br$^\sim$, I$^\sim$, H$^\sim$, CN$^\sim$ and SCN$^\sim$ |
| 7 | CO, NO | carbon monoxide and nitrous oxide |

TABLE 2

| Substituent Group | Type | Definition of R |
|---|---|---|
| A | alkyl and substituted alkyl | 1°, 2°, 3° and cyclic contg. 1-10 carbons where substituents are selected from halo, hydroxy, cyano, amido, amino, mono- and dialkylamino, mono- and diaryl amino, mercapto, sulfonyloxy, alkoxy, thioalkoxy, aryloxy, thioaryloxy, carboxy, alkoxycarbonyl, alkyl- and arylsulfinyl, alkyl- and arylphospho, alkyl- and arylphosphono, substituted and unsubstituted aryls, including phenyl, biphenyl, naphthyl, substituted and unsubstituted N- and S-contg. heteroaryl, including pyridyl, pyrryl, piperidinyl, piperazyl, thienyl, tetrahydrothioenyl, and thiazolyl groups |
| B | aryl and substituted aryl | phenyl, biphenyl, naphthyl and anthracenyl where substituents are selected from those in this Table, Substituent Group A |
| C | heterocycles and substituted heterocycles | N- and S-contg. heterocycles as defined in Table 1, Groups 3 and 4, where substituents are selected from those in this Table, Substituent Group A |

TABLE 3

| Bridging Group | Type | Definition of R' |
|---|---|---|
| I | alkylene, substituted alkylene, alkenylene and substituted alkenylene | 1°, 2°, 3° and cyclic, contg. 1-10 carbons where bridging hydrocarbon chain contains 1-4 carbons and where substituents are selected from those in Table 2, Substituent Group A |
| II | arylene and substituted arylene | as defined in Table 2, Substituent Group B, and contg. two coordinating/chelating groups selected from N, P, S, As and Sb in the 1,2-positions for phenyl; in the 1,2-, 1,8- or 2,3- positions for naphthyl; in the 2,2'-, 2,3- or 3,4- positions for biphenyl; or in the 1,2-, 2,3- or 1,9- positions for anthracenyl |
| III | heterocycles and substituted heterocycles | as defined in Table 2, Substituent Group C, and contg. two coordinating/chelating groups selected from N, P, S, As and Sb in any two adjacent positions |

Suitable monodentate equatorial ligands include the following four groupings of organic compounds:

1. arsines, amines, phosphines and stibnines of the structure

where Z is selected from As, N, P and Sb and each R is independently selected from —H or any of the substituents recited in Table 2, Substituent Group A, B or C (as a group, the three R substituents may comprise any combination of —H or the substituents shown in Table 2);

2. thiols an sulfides of the structure

R—S—R where R is as defined above 3. halogens and the pseudohalogens H⁻, CN⁻ and SCN⁻; and 4. carbon monoxide and nitrous oxide.

Suitable bidentate equatorial ligands include the following four groups of organic compounds:

1. amines, arsines, phosphines and stibnines of the structure

where substituted and Z are as defined above and R' is any of the bridging ligands set forth in Table 3;

2. phosphites of the structure

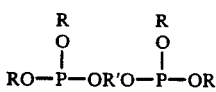

where R and R' are as defined above;

3. thiols and sulfides of the structure

R—S—R'—S—R where R and R' are as defined above; and 4. substituted and unsubstituted nitrogen- and sulfur-containing heterocycles as defined in Table 1, Groups 3 and 4.

Suitable tridentate equatorial ligands include the following four groups of organic compounds:

1. amines, arsines, phosphines and stibnines of the structure

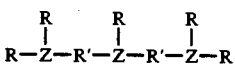

where R, R' and Z are as defined above;

2. phosphites of the structure

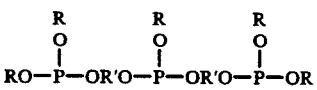

where R and R' are as defined above;

3. thiols and sulfides of the structure

R—S—R'—S—R'—S—R where R and R' are as defined above; and 4. substituted and unsubstituted nitrogen- and sulfur-containing heterocycles as defined in Table 1, Groups 3 and 4.

Suitable tetradentate equatorial ligands include the following six groups of organic compounds:

1. amines, arsines, phosphines, and stibnines of the structure

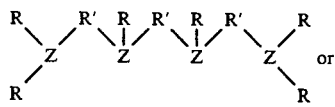

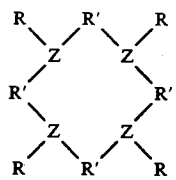

where Z, R and R' are as defined above;

2. phosphites of the structure

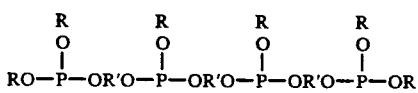

where R and R' are as defined above;

3. thiols and sulfides of the structure

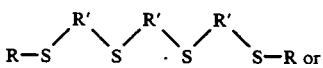

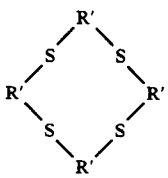

where R and R' are as defined above.

4. substituted and unsubstituted nitrogen- and sulfur-containing heterocycles as defined in Table 1, Groups 3 and 4.

5. substituted and unsubstituted porphyrins of the structure

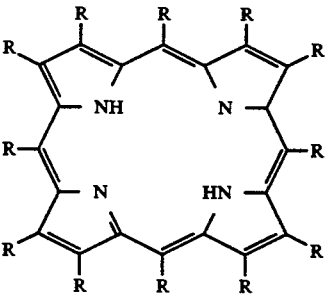

where R is as defined above; and 6. substituted and unsubstituted phthalocyanines of the structure

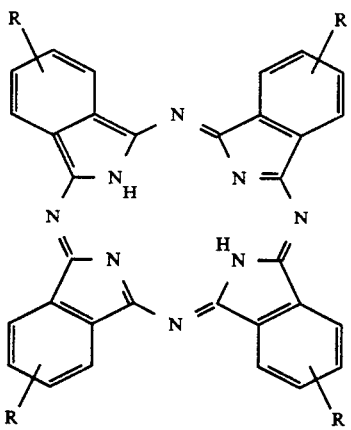

where R is as defined above.

Structural drawings of various equatorial ligands ("L"), where the ligand trans to the bound nitrogen (N₂) is an axial base ("B") coordinated to the metal ("M") are shown below:

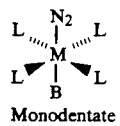

Monodentate

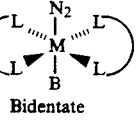

Bidentate

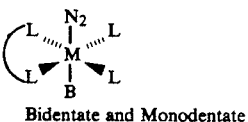

Bidentate and Monodentate

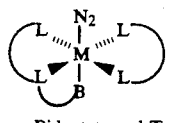

Bidentate and Tridentate where
axial base part of Tridentate

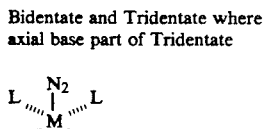

Tridentate and Monodentate where
axial base part of Tridentate

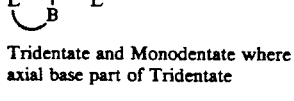

Tetradentate

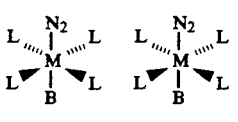

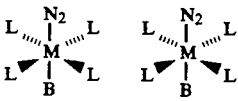

-continued

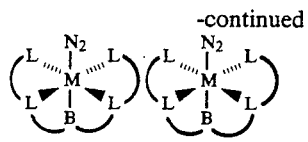

Pentadentate where
axial base is part of Pentadentate

The ligands (including the axial base) may be in any combination such that they provide 5 or 6 coordinating atoms to the complex. Thus, for example, any of the following combinations of ligands are suitable: 5 or 6 monodentates; 3 or 4 monodentates and 1 bidentate; 1 each of a mono-, bi- and tridentate; 1 each of a bi- and tetradentate; 1 each of a mono- and a pentadentate, 2 or 3 monodentates and 1 or 2 tridentate(s); 1 or 2 monodentate and 1 tetradentate; 3 bidentates; 1 pentadentate; and 1 hexadentate.

As mentioned above, the nitrogen-sorbing and -desorbing material may be a solid or a solution. When in the form of a solid, the nitrogen sorption material may be either a solid organometallic complex of the structures discussed above or such an organometallic complex in a relatively inert solid matrix. By an "inert" matrix is meant a material that is substantially non-reactive and does not absorb substantial amounts of nitrogen or other gases in the feed. Preferably, the matrix is highly permeable to gaseous nitrogen so as to permit rapid diffusion therethrough. One class of suitable matrices comprises polymers; examples of such include polydimethylsiloxane, poly(trimethylsilylpropyne), polyurethane, polyvinylalcohol, polyvinylacetate, and cellulose esters. Another class of suitable matrices comprises a porous inorganic material such as an oxide or a ceramic; examples of suitable inorganic oxides include silicon dioxide and titanium dioxide.

The nitrogen sorption material may be used in any of a pressure swing absorption (PSA), a temperature swing absorption (TSA) or a hybrid combination of PSA and TSA. In general, when the nitrogen sorption material is in the form of a solution, it is preferably used in a PSA mode. In a PSA mode, the difference in nitrogen partial pressures between the absorption and desorption steps is preferably in the range of 10 to 400 psi. Nitrogen partial pressure in the desorption step may also be reduced by the use of an inert sweep gas, such as carbon dioxide, argon, hydrogen, helium or methane, preferably in a countercurrent flow mode. Sweep gas may also effectively be generated in situ by the release of other gases (such as methane or other hydrocarbons) absorbed in the solution or by solvent vapor; this release of other sorbed gases effectively lowers the partial pressure of nitrogen. In terms of total pressure, the absorption step is preferably conducted at a total pressure that is at least 20 times the total pressure of the desorption step. When used in a TSA mode, the preferred temperature differential between the absorption and desorption steps is in the range of 20° to 100° C. for economic efficiency to be realized.

The feed gas preferably comprises a mixture of nitrogen and other gases, typically methane and other hydrocarbons, the mixture preferably containing essentially no oxygen, no carbon monoxide, no thiols and no sulfides. Preferred limits on such impurities are such that the partial pressures of the gases are as follows: oxygen $\leq 1$ psi, preferably $10^{-3}$ psi; carbon monoxide $\leq 10$ psi; sulfides and thiols $\leq 10$hu −3 psi. Notwithstanding these preferred lmits, in some cases the nitrogen sorption material may be relatively unaffected by the presence of such impurities and so the feed gas may contain substantial amounts, say, up to 10 vol %, of the same. In general, non-nitrogen components should be soluble in the solvent to a concentration that is less than twice the solubility of the organometallic complex. The feed may be at virtually any temperature in the range of $-20°$ C. to $100°$ C. although in certain cases, mentioned below, higher temperatures may also be used. In general, the preferred temperature range is $0°$ C. to $100°$ C. The amount of nitrogen in the feed stream may be anywhere from 0.1 to 80 vol %. Nitrogen may be mixed with virtually any other gas or combination of gases with the restrictions on impurities noted above. Preferred applications include mixtures of nitrogen with hydrocarbons containing from 1 to 7 carbons, including natural gas, and with hydrocarbons from partial oxidation of hydrocarbons containing from 1 to 7 carbon atoms (from the oxidation of coal and from the oxidative coupling of hydrocarbons). The range of the temperature of the feed may be from $0°$ C. to $200°$ C., preferably $20°$ C. to $150°$ C. The feed may be fed at a pressure of anywhere from 20 psi to 2000 psi.

Over time, the nitrogen-sorbing capacity of the solution may decrease due to a formal oxidation of the metal atom in the organometallic complex. The nitrogen-absorbing capability of the solution may be periodically regenerated by a variety of techniques, including:

(1) formally reducing the metal by heating the solution to $30°$ C. to $180°$ C. while avoiding oxidizing conditions, preferably in the presence of a reducing agent such as hydrogen, magnesium, iron or thiosulfate ion;

(2) stripping the solvent from the solution and then recrystallizing the residual organometallic complex from a suitable solvent under a nitrogen or other inert gas atmosphere; and (3) demetallating the organometallic complex in solution by the addition of a strong acid, extracting the oxidized transition metal into an immiscible organic solvent, then coordination of the reduced transition metal with the solution of the equatorial ligand(s) and axial base, and recrystallizing the regenerated organometallic complex.

In connection with the first regeneration method mentioned above, oxidizing conditions may be avoided by heating the solution (a) under a vacuum of from 0.2 to 20 cmHg for about 1 to 48 hours, (b) in an inert atmosphere such as nitrogen or argon for about 1 to 72 hours, or (c) in a reducing atmosphere such as hydrogen for from about 1 to 72 hours, with or without the presence of a reduction catalyst such as a platinum group metal.

In connection with the second regeneration method, the inactive organometallic complex may be isolated from the solvent by vacuum or atmospheric distillation of the solvent, and the residual organometallic complexes recrystallized from an appropriate solvent.

In connection with the third method of regeneration, suitable strong acids include hydrochloric acid, sulfuric acid, and trifluoroacetic acid. The oxidized metal may be extracted into an immiscible organic solvent, such as toluene and other aromatic solvents, and hexane and other aliphatic solvents, by addition of an organic-soluble metal extractant, such as dialkylphosphoric acids, alkylamines, quaternary alkylamines, and alkyl-$\beta$-diketones, to the aromatic or aliphatic solvent. Suitable solvents for recrystallization of the organometallic complex include water, methanol, ethanol, tetrahydrofuran, and acetonitrile.

Referring now to the drawings, wherein like numerals refer to the same elements, use of the solution of the present invention in a PSA mode is depicted in FIG. 1. There, a nitrogen-containing feed 10 is introduced into a conventional gas-liquid absorption column 20 so that the gas is efficiently contacted with the solution of the present invention. Within the absorption column 20, nitrogen is selectively absorbed by the solution, resulting in a reduction in the nitrogen concentration in the "product" gas 25 exiting the column (it being understood that virtually any gas other than nitrogen, depending upon the desired separation, could be regarded as the product gas). The residence time of the solvent in the absorption column 20 is on the order of a few minutes and generally should be sufficiently long to achieve nitrogen binding to at least 10 mol % of the organometallic absorbent. The column should be sized sufficiently to accommodate the requisite volume and flow rate of liquid absorbent to have sufficient contact time for nitrogen to be absorbed by the liquid. In place of the absorption column 20, other gas-liquid contactors may be utilized, such as membrane contactors in the form of hollow fiber modules. The nitrogen-complexed liquid absorbent 28 is passed to a stripping column 40 in which nitrogen is desorbed from the liquid absorbent. For nitrogen desorption to occur in the stripping column, the partial pressure of nitrogen in the nitrogen-containing stream 45 exiting the stripping column 40 must be less than the partial pressure of nitrogen in the product stream 25 exiting the absorption column 20. This condition is met by operating the stripping column 40 at a reduced pressure relative to the absorption column 20 (typically near 0 psig total pressure) or by using a sweep stream 35 to maintain low nitrogen partial pressures in the nitrogen-containing stream 45 exiting the stripping column 40. The nitrogen-containing stream 45 desorbed from the liquid absorbent exits the stripping column 40 at substantially the same pressure as that prevailing in the stripping column, which is typically near 0 psig total pressure. In some cases the desorbed nitrogen from the nitrogen-containing stream 45 may be the end product of the separation process. After nitrogen is desorbed from the liquid absorbent in the stripping column 40, the nitrogen-stripped liquid absorbent 48 is returned to the absorption column 20 by use of a pump 30, and the cycle is repeated.

Figure 2:
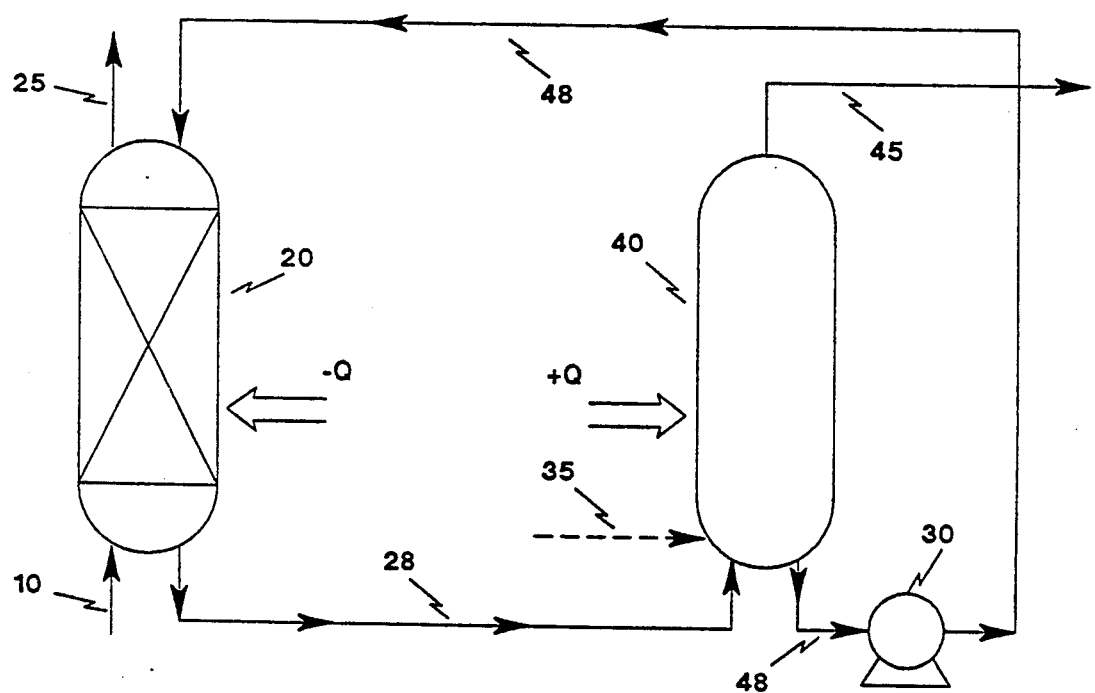
FIG. 2 is a schematic of an exemplary hybrid pressure/temperature swing absorption/desorption process of the present invention.

Use of the nitrogen-sorbing and -desorbing solution of the present invention in a hybrid PSA/TSA mode is shown schematically in FIG. 2. There, the system is operated in generally the same manner as described for FIG. 1, except that the stripping column 40 is operated at an elevated temperature relative to the absorption column 20, the addition of heat to the stripping column 40 being depicted schematically by the symbol "+Q". Alternatively, the absorption column 20 may be cooled relative to the stripping column 40, this being schematically depicted by the symbol "−Q". This hybrid mode of operation is useful in compensating for the fact that the nitrogen-binding capacity of the liquid absorbent for a given nitrogen partial pressure decreases with increasing temperature inasmuch as the nitrogen-binding is typically a somewhat exothermic reaction. As a result, the nitrogen partial pressure in equilibrium with the nitrogen-containing absorbent will increase with increasing temperature. For nitrogen desorption to occur in the stripping column 40, the concentration in the absorbent liquid in equilibrium with product gas 25 exiting the absorption column 20 at the temperature and pressure prevailing therein must exceed the concentration of nitrogen in the absorbent in equilibrium with the nitrogen in nitrogen-containing stream 45 at the temperature and pressure prevailing in the stripping column 40. The advantage of the hybrid PSA/TSA mode over the purely PSA mode is that in the former, nitrogen desorption can be achieved in the stripping column 20 at nitrogen partial pressures greater than those allowed in the strictly PSA mode. As with the PSA mode, the hybrid PSA/TSA mode may be used to achieve nitrogen desorption in the stripping column 40 by either operating the stripping column at reduced pressure relative to the absorption column or by the use of a sweep gas. However, since the stripping column is at a higher temperature than the absorption column, the stripping column need not be at a lower pressure but may be at the same or even higher pressure than the absorption column. Another advantage of operating the stripping column at elevated temperature is that an increase in the rate of nitrogen desorption from the liquid absorbent occurs, resulting in a decrease in the residence time required for the liquid absorbent in the stripping column.

Figure 3:
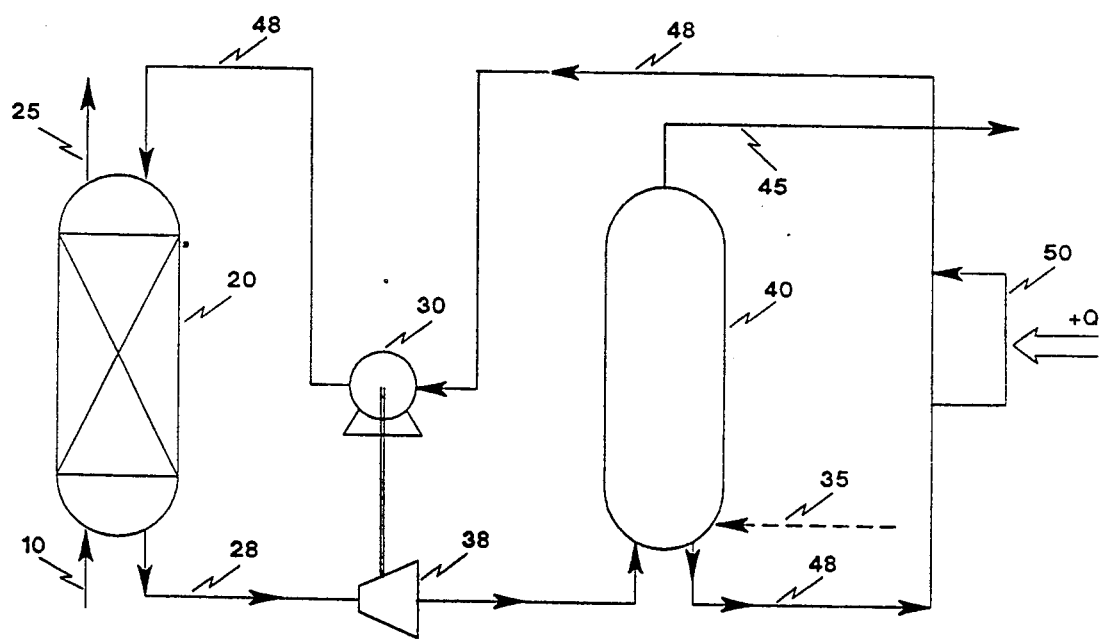
FIG. 3 is a schematic of the exemplary process depicted in FIG. 1 wherein a pressure-reducing turbine and a regeneration loop are included.

FIG. 3 depicts the inclusion of a regeneration loop 50 wherein the nitrogen-stripped liquid sorbent 48 is treated by one of the methods described above to regenerate its nitrogen-sorption capacity, as well as the inclusion of a pressure-reducing turbine 38 to recover energy otherwise lost, the energy being used to drive the liquid pump 30. A preferred type of pressure-reducing or power recovery turbine is that which is commercially available from Sulzer Bingham of Portland, Oreg.

When the nitrogen-absorbing and -desorbing material is a solid, the material can be used in essentially the same manner as that described above for liquid absorbents except that the gas-liquid contactors would constitute fluidized beds with the solid material and either feed gas or desorbed gas from the stripper preferably flowing countercurrently. The solid may also be used in conventional pressure-swing or temperature-swing processes in a manner similar to the way zeolites or carbon molecular sieves are used to separate gas mixtures such as in the production of nitrogen or oxygen from air.

EXAMPLE 1

Figure 4:
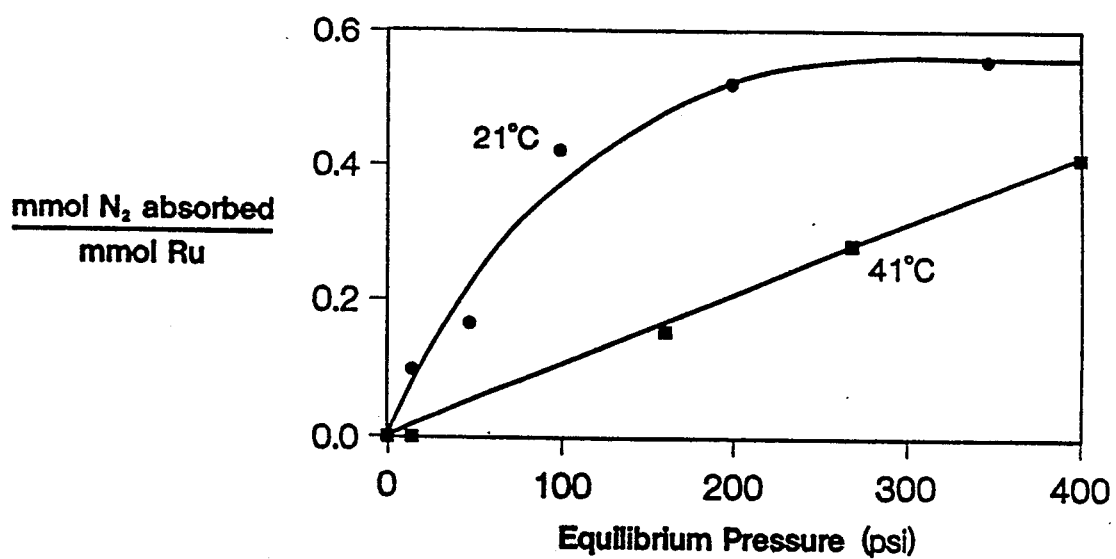
FIGS. 4 and 5 are graphs of isotherms observed for two exemplary sorption compositions of the present invention.

A 0.25M solution of the organometallic complex [Ru(H$_2$O)(Hedta)]$^-$ in water (as the potassium salt) was used to determine nitrogen-binding isotherms at 21° C. and at 41° C. (Hedta is monoprotonated ethylene diamine tetraacetate). This was accomplished by measuring the uptake of nitrogen by the solution over a range of nitrogen pressures. The resulting isotherms are shown in FIG. 4. From these isotherms, the equilibrium constant of nitrogen binding is calculated to be 0.08 (psi-M)$^{-1}$ at 21° C. and 0.024 (psi-M)$^{-1}$ at 41° C. These equilibrium constants are based on the following assumed nitrogen-binding reaction:

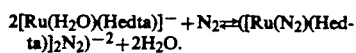

$$2[Ru(H_2O)(Hedta)]^- + N_2 \rightleftharpoons \{[Ru(N_2)(Hedta)]_2 N_2\}^{-2} + 2H_2O.$$

These data show that at 21° C. and high nitrogen pressures (300 to 350 psi), the solution of [Ru(H$_2$O)(Hedta)]$^-$ absorbs approximately 0.5 mmole of nitrogen per mmole of the complex. However, at 21° C. and low nitrogen pressure (<50 psi), the solution absorbs <0.2 mmole nitrogen per mmole of the complex. Thus, an aqueous solution of this organometallic complex can be used to remove nitrogen from a high-pressure gas stream by first permitting the solution to absorb nitrogen at high pressure, then pumping the nitrogen-laden solution to a stripping column at low pressure to allow nitrogen to desorb from the solution. For example, at a solution temperature of about 21° C., a swing in nitrogen partial pressure from 350 psi in the absorption stage to 50 psi in the desorption stage will result in the net removal of more than 0.3 mmole of nitrogen per mmole of [Ru (Hedta)]$^-$.

Referring again to FIG. 4, the 41° C. isotherm is shifted below the 21° C. isotherm because coordination of nitrogen to the organometallic complex is an exothermic process, i.e., as the temperature increases, the fraction of nitrogen coordinated to the organometallic complex decreases. This property may be used to increase the amount of nitrogen that is desorbed from the nitrogen-laden solution. Accordingly, a hybrid PSA-TSA process may be used to remove nitrogen from a gas stream by permitting the complex-containing solution to absorb nitrogen at high pressure at about 21° C., removing the nitrogen-laden solution, and heating it to about 41° C., then pumping the nitrogen-laden solution to a stripping column at low pressure, thereby allowing nitrogen to desorb from the solution. For example, by maintaining the nitrogen partial pressure at about 350 psi and the temperature at 21° C. in the absorption column and at about 50 psi and 40° C. in the stripping column, about 0.45 mmole nitrogen per mmol [Ru (Hedta)]$^-$ may be removed from the feed gas.

EXAMPLE 2

Figure 5:
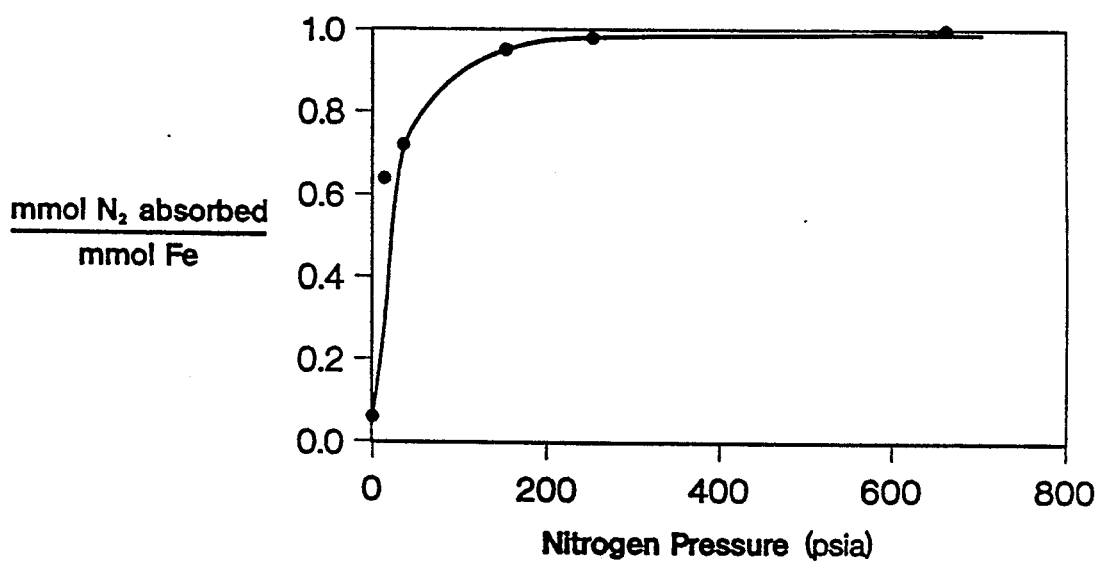

The nitrogen-binding isotherm at 21° C. of a 0.02M solution of the organometallic complex [Fe(H)(diphos)$_2$]$^+$ (diphos=Ph$_2$PCH$_2$CH$_2$PPh$_2$) was determined. This was accomplished by measuring, as a function of nitrogen pressure, the intensity of the infrared absorption band corresponding to the nitrogen-nitrogen stretch at 2122 cm$^{-1}$. The results are shown in FIG. 5. From this isotherm the equilibrium constant for nitrogen-binding is calculated to be 0.15 (psi-M)$^{-1}$. The value of the equilibrium constant is based on the following assumed nitrogen-binding reaction:

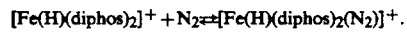

$$[Fe(H)(diphos)_2]^+ + N_2 \rightleftharpoons [Fe(H)(diphos)_2(N_2)]^+.$$

Since [Fe(H)(diphos)$_2$] binds nitrogen more tightly than [Ru(H$_2$O)(Hedta)]$^-$, the nitrogen can be desorbed only at relatively low nitrogen partial pressure and/or elevated temperatures. For example, to achieve a net removal of 0.5 mmole nitrogen per mmole [Fe(H)(diphos)$_2$]$^+$ at a temperature of about 21° C., the nitrogen partial pressure in the desorption column would have to be about 7 psia or less given a nitrogen pressure in the absorption column of at least 200 psig. As is the case with [Ru(H$_2$O)(Hedta)]$^-$, desorption of nitrogen from a solution of [Fe(H)(diphos)$_2$]$^+$ can be achieved at higher nitrogen pressures if the solution is heated (e.g., to about 41° C.) during the desorption of nitrogen.

EXAMPLE 3

To demonstrate that nitrogen is selectively absorbed from a gas mixture containing nitrogen and methane, a 0.36M (7.2 mmole) aqueous solution of the organometallic complex [Ru(H$_2$O)(Hedta)]$^-$ (as the potassium salt) was exposed to a 7.5% nitrogen-containing nitrogen/methane gas mixture at 518 psi. Nitrogen partial pressure loss demonstrated that approximately 0.24 mmole of nitrogen gas was complexed or absorbed by the complex-containing solution. Isolation of the remainder of the gas mixture and analysis by gas liquid chromatography demonstrated its composition to be 7.0±0.1% nitrogen, indicating that 0.5% (0.19 mmole) nitrogen was desorbed from the solution.

EXAMPLE 4

The organometallic complex-containing solution of the present invention was demonstrated to be regenerable. A 0.4M aqueous solution of the organometallic complex [Ru($H_2O$)(Hedta)]$^-$ was exposed to air for 24 hours. Aerobic oxidation of [Ru($H_2O$)(Hedta)]$^-$ is reported in the literature to yield [Ru($H_2O$)(Hedta)], which does not absorb nitrogen. That is, contact with air results in oxidation of Ru from the +2 to the +3 oxidation state. Subsequently the oxidized solution was contacted with the reducing agent magnesium to regenerate [Ru($H_2O$)(Hedta)]$^-$. The regenerated solution was found to reversibly absorb nitrogen according to the binding isotherm shown in FIG. 4 and also to selectively absorb nitrogen from $N_2/CH_4$ as described in Example 3.

EXAMPLE 5

The capability of the organometallic complex of the present invention in a solid form to reversibly bind nitrogen was demonstrated. A 1.86 g (1.99 mmole) portion of the solid organometallic complex Mo(triphos)[P($CH_3$)$_2$($C_6H_5$)]$_2$ (triphos=($C_6H_5$)$_2$PCH$_2$CH$_2$P($C_6H_5$)CH$_2$CH$_2$P($C_6H_5$)$_2$) was exposed to a stream of pure nitrogen and indicated nitrogen absorption by turning a bright orange color. The solid complex was then heated under vacuum (1 torr) for 3 days at 50° C., causing the bright-orange solid to change to deep orange-brown. This color change is indicative of the complex desorbing nitrogen and forming the putative five-coordinate complex Mo(-triphos)[P($CH_3$)$_2$($C_6H_5$)]. A portion (1.59±0.01 g or 1.76±0.01 mmole) of this orange-brown solid organometallic complex was then placed in Fischer-Porter pressure bottle under 32 psig nitrogen at 20°±2° C. Over a 25 hour reaction period, 1.22±0.14 mmole nitrogen was absorbed by the solid complex (corresponding to a 4.5±0.5 psig nitrogen partial pressure loss) and the initial bright orange color of the complex was regenerated. The solid complex was then weighed at 1.62±0.01 g, thus exhibiting an overall weight increase of 0.03±0.02 g, which corresponds to an absorption of 1.1±0.7 mmole nitrogen.

The composition of the present invention may also be used strictly in the absorption mode, e.g., as a nitrogen detector or a nitrogen getter to remove small amounts of nitrogen from inert gas streams such as an argon gas stream.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A process for the separation of nitrogen comprising the steps:
   (a) absorbing nitrogen from a nitrogen-containing feed stream containing from 0.1 to 80 vol % nitrogen by contacting said feed stream with a composition comprising a solvent and an organometallic complex, said organometallic complex consisting essentially of a transition metal selected from Mo, W and a metal from Groups 7, 8 and 9, and one or more ligands capable of providing five or six coordinating atoms to said organometallic complex, said solvent being capable of dissolving said organometallic complex to $\geq$0.1M; and
   (b) desorbing nitrogen from said composition to a product stream wherein the conditions for conducting steps (a) and (b) are selected from one of
      (i) step (a) is conducted at a lower temperature than step (b);
      (ii) step (a) is conducted at a nitrogen partial pressure that is greater than the nitrogen partial pressure of step (b); and
      (iii) both (i) and (ii).

2. A process for the separation of nitrogen comprising the steps:
   (a) absorbing nitrogen from a nitrogen-containing feed stream containing from 0.1 to 80 vol % nitrogen by contacting said feed stream with a solid composition comprising a solid inert matrix and an organometallic complex, the concentration of said organometallic complex being $\geq$0.1M relative to said matrix, said organometallic complex consisting essentially of a transition metal selected from Mo, W and a metal from Groups 7, 8 and 9, and one or more ligands capable of providing five or six coordinating atoms to said organometallic complex; and
   (b) desorbing nitrogen from said composition to a product stream, wherein the conditions for conducting steps (a) and (b) are selected from one of
      (i) step (a) is conducted at a lower temperature than step (b);
      (ii) step (a) is conducted at a nitrogen partial pressure that is greater than the nitrogen partial pressure of step (b); and
      (iii) both (i) and (ii).

3. The process of claim 1 or 2 wherein said one or more ligands comprises a ligand selected from a monodentate, a bidentate, a tridentate, a tetradentate, a pentadentate, and a hexadentate ligand.

4. The process of claim 1 or 2 wherein said composition includes an axial base as one of the ligands.

5. The process of claim 1 or 2 wherein the difference between the temperatures of steps (a) and (b) is 20° to 100° C.

6. The process of claim 1 or 2 wherein the difference between the nitrogen partial pressures of steps (a) and (b) is 10 to 400 psi.

7. The process of claim 1 or 2 wherein step (a) is conducted at a total pressure that is at least 20 times the total pressure in step (b).

8. The process of claim 1 or 2 wherein step (a) is conducted at a lower temperature than the temperature of step (b).

9. The process of claim 8 wherein the difference between the temperatures of steps (a) and (b) is 20° to 100° C.

10. The process of claim 1 or 2 wherein step (b) is conducted with a sweep gas.

11. The process of claim 10 wherein said sweep gas is selected from argon, carbon dioxide, helium, hydrogen, and methane.

12. The process of claim 1 or 2 wherein said feed stream contains oxygen in an amount such that the oxygen partial pressure in said feed stream is ≦1 psi.

13. The process of claim 1 or 2 wherein said feed stream comprises nitrogen and hydrocarbon gas predominantly containing 1 to 7 carbon atoms.

14. The process of claim 13 wherein said hydrocarbon gas is natural gas.

15. The process of claim 13 wherein said hydrocarbon gas is from a partial oxidation of hydrocarbons.

16. The process of claim 13 wherein said hydrocarbon gas is from partial oxidation of coal.

17. The process of claim 13 wherein said hydrocarbon gas is from oxidative coupling of hydrocarbons.

18. The process of claim 1, including periodic regeneration of the nitrogen-absorbing capability of said solution.

19. The process of claim 18 wherein said regeneration is accomplished by heating said solution in an inert atmosphere.

20. The process of claim 18 wherein said regeneration is accomplished by heating said solution in the presence of a reducing agent.

21. The process of claim 20 wherein said reducing agent is selected from hydrogen, iron, magnesium and a platinum group metal.

* * * * *

UNITED STATES PATENT AND TRADEMARK OFFICE
CERTIFICATE OF CORRECTION

PATENT NO. : 5,225,174   Page 1 of 3

DATED : July 6, 1993

INVENTOR(S) : Friesen, Babcock, Edlund, Miller

It is certified that error appears in the above-indentified patent and that said Letters Patent is hereby corrected as shown below:

Col. 2, line 29: delete "22"

Col. 3, lines 57 and 59: delete "F~, Cl~, Br~, I~, H~, CN~ and SCN~" and insert -- $F^-$, $Cl^-$, $Br^-$, $I^-$, $H^-$, $CN^-$ and $SCN^-$ --

Col. 5, line 4: delete "an" and insert -- and --

Col. 5, line 8: insert -- ; -- after above

Col. 5, line 21: delete "substituted" and insert -- R --

UNITED STATES PATENT AND TRADEMARK OFFICE
CERTIFICATE OF CORRECTION

PATENT NO. : 5,225,174

DATED : July 6, 1993

INVENTOR(S) : Friesen, Babcock, Edlund, Miller

It is certified that error appears in the above-indentified patent and that said Letters Patent is hereby corrected as shown below:

Col. 7, line 48 through col. 8, line 7: correct the structural drawings as shown below:

Bidentate and Monodentate

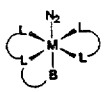

Bidentate and Tridentate where axial base part of Tridentate

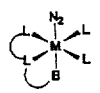

Tridentate and Monodentate where axial base part of Tridentate

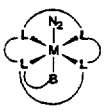 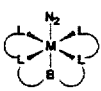

Tetradentate

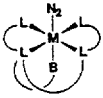 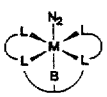

Pentadentate where axial base is part of Pentadentate

UNITED STATES PATENT AND TRADEMARK OFFICE
CERTIFICATE OF CORRECTION

PATENT NO. : 5,225,174

DATED : July 6, 1993

INVENTOR(S) : Friesen, Babcock, Edlund, Miller

It is certified that error appears in the above-indentified patent and that said Letters Patent is hereby corrected as shown below:

Col. 8, line 68: delete " $\leq$10hu-3 and insert -- $\leq 10^{-3}$ --.

Signed and Sealed this

Thirtieth Day of August, 1994

Attest:

Attesting Officer

BRUCE LEHMAN

Commissioner of Patents and Trademarks